(12) United States Patent
Crowell et al.

(10) Patent No.: US 7,972,810 B2
(45) Date of Patent: Jul. 5, 2011

(54) PRODUCTION OF GLYCOPROTEINS USING MANGANESE

(75) Inventors: Christopher K. Crowell, Erie, CO (US); Gustavo E. Grampp, Boulder, CO (US)

(73) Assignee: Amgen Inc., Thousand Oaks, CA (US)

( * ) Notice: Subject to any disclaimer, the term of this patent is extended or adjusted under 35 U.S.C. 154(b) by 975 days.

(21) Appl. No.: 11/634,506

(22) Filed: Dec. 6, 2006

(65) Prior Publication Data
US 2007/0161084 A1 Jul. 12, 2007

Related U.S. Application Data

(60) Provisional application No. 60/748,880, filed on Dec. 8, 2005.

(51) Int. Cl.
*C12N 15/00* (2006.01)
*C12N 5/00* (2006.01)
*C07K 14/00* (2006.01)
*C07K 14/505* (2006.01)

(52) U.S. Cl. .................. 435/69.1; 435/325; 530/395

(58) Field of Classification Search .................. None
See application file for complete search history.

(56) References Cited

U.S. PATENT DOCUMENTS

| | | | |
|---|---|---|---|
| 4,667,016 A | 5/1987 | Lai et al. | |
| 4,703,008 A | 10/1987 | Lin | |
| 5,459,031 A | 10/1995 | Blumen et al. | |
| 5,808,006 A * | 9/1998 | Builder et al. | 530/399 |
| 2004/0053398 A1* | 3/2004 | Murray | 435/252.3 |

FOREIGN PATENT DOCUMENTS

| | | |
|---|---|---|
| EP | 1085083 A1 | 3/2001 |
| WO | WO 91/05867 | 5/1991 |
| WO | WO 95/05465 | 2/1995 |
| WO | WO 98/08934 | 3/1998 |
| WO | WO 00/24893 | 5/2000 |
| WO | WO 01/81405 | 11/2001 |

OTHER PUBLICATIONS

Raju et al. Glycoengineering of Therapeutic glycoproteins: In vitro galactosylation and sialylation of glycoproteins with terminal N-acetylglucosamine and galactose residues. Biochemistry 40:8868-8876 (2001).*
Millot et al. The granulocyte colony-stimulating factor receptor supports erythroid differentiation in the absence of erythropoietin receptor or Stat5. British Journal of Haematology, 112:449-458 (2001).*
Ketley et al. Abstract. Hemopoietic growth factors. Postgraduate Medical Journal, vol. 73(858):215-221 (1997).*
Deeg et al. Abstract. Soluble TNF receptor fusion protein (TNFR:Fc; Enbrel) in the treatment of patients with myelodysplastic syndrome (MDS). Blood vol. 96/No. 11, part I, pp. 146 a. (Nov. 16, 2000).*
Dorner et al. Analysis of Synthesis, Processing and Secretion of Proteins Expressed in Mammalian Cells. Methods in Enzymology vol. 185:577-596 (1990).*
Ashwell et al., "Carbohydrate-specific receptors of the liver," *Ann. Rev. Biochem.*, 51(1):531-554 (1982).
Cotes et al., "Bio-assay of erythropoietin in mice made polycythaemic by exposure to air at a reduced pressure," *Nature*, 191:1065-1067 (1961).
Couto et al., "Cloning and expression in *Escherichia coli* of a yeast mannosyltransferase from the asparagine-linked glycosylation pathway," *J. Biol. Chem.*, 259(1):378-382 (1984).
Darling et al., "Glycosylation of erythropoietin affects receptor binding kinetics: Role of electrostatic interactions," *Biochem.*, 41(49):14524-14531 (2002).
Delorme et al., "Role of glycosylation on the secretion and biological activity of erythropoietin," *Biochem.*, 31:9871-9876 (1992).
Elliott et al., "Structural requirements for addition of O-linked carbohydrate to recombinant erythropoietin," *Biochem.*, 33(37):11237-11245 (1994).
Elliott et al., "Control of rHuEPO biological activity: The role of carbohydrate," *Exp. Hematol.*, 32(12):1146-1155 (2004).
Goldberg et al., "Oxygen sensing and erythropoietin gene regulation in a human hepatoma cell line," In: *Regulation of Erythropoietin Production, The Red Cell: Seventh Ann Arbor Conference*, pp. 467-489 © 1989, Alan R. Liss, Inc.
Goochee et al., "The oligosaccharides of glycoproteins: Bioprocess factors affecting oligosaccharide structure and their effect on glycoprotein properties," *Bio/Technology*, 9(12):1347-1355 (1991).
Jensen et al., "The biosynthesis of oligosaccharide-lipids," *J. Biol. Chem.*, 256(24)12899-12904 (1981).
Kaufman et al., "Depletion of manganese within the secretory pathway inhibits O-linked glycosylation in mammalian cells," *Biochem.*, 33(33):9813-9819 (1994).
Kelleher et al., "Oligosaccharyltransferase activity is associated with a protein complex composed of ribophorins I and II and a 48 kd protein," *Cell*, 69(1):55-65 (1992).
Kelleher et al., "DAD1, the defender against apoptotic cell death, is a subunit of the mammalian oligosaccaryltransferase," *Proc. Natl. Acad. Sci. USA*, 94(10):4994-4999 (1997).
Kelleher et al., "Oligosaccharyltransferase isoforms that contain different catalytic STT3 subunits have distinct enzymatic properties," *Mol. Cell*, 12(1):101-111 (2003).
Powell et al., "Metal ion activation of galactosyltransferase," *J. Biol. Chem.*, 251(12):3645-3652 (1976).
Sharma et al., "Solubilization and characterization of the initial enzymes of the dolichol pathway from yeast," *Eur. J. Biochem.*, 126(2):319-325 (1982).
Sugiura et al., "Purification and characterization of UDP-GaINAc: Polypeptide N-acetylgalactosamine transferase from an ascites hepatoma, AH 66," *J. Biol. Chem.*, 257(16):9501-9507 (1982).
Takeuchi et al., "Comparative study of the asparagine-linked sugar chains of human erythropoietins purified from urine and the culture medium of recombinant chinese hamster ovary cells," *J. Biol. Chem.*, 263(8):3657-3663 (1988).
Takeuchi et al., "Relationship between sugar chain structure and biological activity of recombinant human erythropoietin produced in Chinese hamster ovary cells," *Proc. Natl. Acad. Sci. USA*, 86(20):7819-7822 (1989).
Witsell et al., "Divalent activation of galactosyltransferase in native mammary golgi vesicles," *J. Biol. Chem.*, 265(26):15731-15737 (1990).
Zanette et al., "Evaluation of phenylboronate agarose for industrial-scale purification of erythropoietin from mammalian cell cultures," *J. Biotech.*, 101(3):275-287 (2003).
Crowell et al. "Amino acid and manganese supplementation modulates the glycosylation state of erythropoietin in a CHO culture system," *Biotechnology and Bioengineering* 96: 538-549, 2007.

* cited by examiner

*Primary Examiner* — Marianne P Allen
*Assistant Examiner* — Regina M DeBerry
(74) *Attorney, Agent, or Firm* — Michael G. Penn

(57) ABSTRACT

Culture media comprising manganese and methods of culturing cells to improve sialylation and glycosylation of glycoproteins are provided.

17 Claims, 10 Drawing Sheets

SEQUENCE LISTING

```
<160> NUMBER OF SEQ ID NOS: 3

<210> SEQ ID NO 1
<211> LENGTH: 1725
<212> TYPE: DNA
<213> ORGANISM: Homo sapiens

<400> SEQUENCE: 1
gaattccctg tggaatgtgt gtcagttagg gtgtggaaag tccccaggct ccccagcagg     60
cagaagtatg caaagcatgc atctcaatta gtcagcaacc aggtgtggaa agtccccagg    120
ctccccagca ggcagaagta tgcaaagcat gcatctcaat tagtcagcaa ccatagtccc    180
gcccctaact ccgcccatcc cgcccctaac tccgcccagt tccgcccatt ctccgcccca    240
tggctgacta atttttttta tttatgcaga ggccgaggcc gcctcggcct ctgagctatt    300
ccagaagtag tgaggaggct tttttggagg cctaggcttt tgcaaaaagc tggtcgagga    360
actgaaaaac cagaaagtta actggtaagt ttagtctttt tgtcttttat ttcaggtccc    420
ggatccggtg gtggtgcaaa tcaaagaact gctcctcagt ggatgttgcc tttacttcta    480
ggcctgtacg gaagtgttac ttctgctcta aaagctgctg caacaagctg gtcgagatcc    540
taggtcaccc ggcgcgcccc aggtcgctga gggacccccgg ccaggcgcgg agatgggggt    600
gcacgaatgt cctgcctggc tgtggcttct cctgtccctg ctgtcgctcc ctctgggcct    660
cccagtcctg ggcgccccac cacgcctcat ctgtgacagc cgagtcctgg agaggtacct    720
cttggaggcc aaggaggccg agaatatcac gacgggctgt aatgaaacgt gcagcttgaa    780
tgagaatatc actgtcccag acaccaaagt taatttctat gcctggaaga ggatggaggt    840
cgggcagcag gccgtagaag tctggcaggg cctggccctg ctgtcggaag ctgtcctgcg    900
gggccaggcc ctgttggtca actcttccca ggtgaatgag accctgcagc tgcatgtgga    960
taaagccgtc agtggccttc gcagcctcac cactctgctt cgggctctgg gagcccagaa   1020
ggaagccatc tcccctccag atgcggcctc agctgctcca ctccgaacaa tcactgctga   1080
cactttccgc aaactcttcc gagtctactc caatttcctc cggggaaagc tgaagctgta   1140 cacagggggag gcctgcagga cagggacag atgaccaggt gtgtccacct gggcatatcc   1200
accacctccc tcaccaacat tgcttgtgcc acaccctccc ccgccactcc tgaaccccgt   1260
cgaggggctc tcagctcagc gccagcctgt cccatggaca ctccagtgcc agcaatgaca   1320
tctcagggcc cagaggaact gtccagagag caactctgag atctcgacca tgggaaatgt   1380
cagagtggag aaccacaccg agtgccactg cagcacttgt tattatcaca aatcctaata   1440
```

```
gtttgcagtg ggccttgctg atgatggctg acttgctcaa aaggaaaatt aatttgtcca    1500
gtgtctatgg ctttgtgaga taaaaccctc cttttccttg ccataccatt tttaacctgc    1560
tttgagaata tactgcagct ttattgcttt tctccttatc ctacaatata atcagtagtc    1620
ttgatctttt catttggaat gaaatatggc atttagcatg accataaaaa gctgattcca    1680
ctggaaataa agtcttttaa atcatcactc tatcactgaa ttcta                    1725
```

```
<210> SEQ ID NO 2
<211> LENGTH: 193
<212> TYPE: PRT
<213> ORGANISM: Homo sapiens
<220> FEATURE:
<221> NAME/KEY: mat_peptide
<222> LOCATION: (28)..(192)

<400> SEQUENCE: 2
```

Met Gly Val His Glu Cys Pro Ala Trp Leu Trp Leu Leu Ser Leu
            -25                 -20                 -15

Leu Ser Leu Pro Leu Gly Leu Pro Val Leu Gly Ala Pro Pro Arg Leu
    -10                  -5                  -1   1               5

Ile Cys Asp Ser Arg Val Leu Glu Arg Tyr Leu Leu Glu Ala Lys Glu
                10                  15                  20

Ala Glu Asn Ile Thr Thr Gly Cys Asn Glu Thr Cys Ser Leu Asn Glu
            25                  30                  35

Asn Ile Thr Val Pro Asp Thr Lys Val Asn Phe Tyr Ala Trp Lys Arg
            40                  45                  50

Met Glu Val Gly Gln Gln Ala Val Glu Val Trp Gln Gly Leu Ala Leu
    55                  60                  65

Leu Ser Glu Ala Val Leu Arg Gly Gln Ala Leu Leu Val Asn Ser Ser
70                  75                  80                  85

Gln Val Asn Glu Thr Leu Gln Leu His Val Asp Lys Ala Val Ser Gly
                90                  95                  100

Leu Arg Ser Leu Thr Thr Leu Leu Arg Ala Leu Gly Ala Gln Lys Glu
            105                 110                 115

Ala Ile Ser Pro Pro Asp Ala Ala Ser Ala Ala Pro Leu Arg Thr Ile
            120                 125                 130

Thr Ala Asp Thr Phe Arg Lys Leu Phe Arg Val Tyr Ser Asn Phe Leu
    135                 140                 145

Arg Gly Lys Leu Lys Leu Tyr Thr Gly Glu Ala Cys Arg Thr Gly Asp
150                 155                 160                 165

Arg

```
<210> SEQ ID NO 3
<211> LENGTH: 193
<212> TYPE: PRT
<213> ORGANISM: Homo sapiens
<220> FEATURE:
<221> NAME/KEY: mat_peptide
<222> LOCATION: (28)..(192)

<400> SEQUENCE: 3
```

Met Gly Val His Glu Cys Pro Ala Trp Leu Trp Leu Leu Ser Leu
            -25                 -20                 -15

Leu Ser Leu Pro Leu Gly Leu Pro Val Leu Gly Ala Pro Pro Arg Leu
    -10                  -5                  -1   1               5

Ile Cys Asp Ser Arg Val Leu Glu Arg Tyr Leu Leu Glu Ala Lys Glu
                10                  15                  20

-continued

| | | | | | | | | | | | | | |
|---|---|---|---|---|---|---|---|---|---|---|---|---|---|
|Ala|Glu|Asn|Ile<br>25|Thr|Thr|Gly|Cys|Ala<br>30|Glu|His|Cys|Ser|Leu<br>35|Asn|Glu|
|Asn|Ile|Thr<br>40|Val|Pro|Asp|Thr|Lys<br>45|Val|Asn|Phe|Tyr|Ala<br>50|Trp|Lys|Arg|
|Met|Glu<br>55|Val|Gly|Gln|Gln|Ala<br>60|Val|Glu|Val|Trp|Gln<br>65|Gly|Leu|Ala|Leu|
|Leu<br>70|Ser|Glu|Ala|Val|Leu<br>75|Arg|Gly|Gln|Ala|Leu<br>80|Leu|Val|Asn|Ser|Ser<br>85|
|Gln|Pro|Trp|Glu|Pro<br>90|Leu|Gln|Leu|His|Val<br>95|Asp|Lys|Ala|Val|Ser<br>100|Gly|
|Leu|Arg|Ser|Leu<br>105|Thr|Thr|Leu|Leu|Arg<br>110|Ala|Leu|Gly|Ala|Gln<br>115|Lys|Glu|
|Ala|Ile|Ser<br>120|Pro|Pro|Asp|Ala|Ala<br>125|Ser|Ala|Ala|Pro|Leu<br>130|Arg|Thr|Ile|
|Thr|Ala<br>135|Asp|Thr|Phe|Arg|Lys<br>140|Leu|Phe|Arg|Val|Tyr<br>145|Ser|Asn|Phe|Leu|
|Arg<br>150|Gly|Lys|Leu|Lys|Leu<br>155|Tyr|Thr|Gly|Glu|Ala<br>160|Cys|Arg|Thr|Gly|Asp<br>165|
|Arg|

PRODUCTION OF GLYCOPROTEINS USING MANGANESE

The present application claims benefit under 35 U.S.C. §119 of U.S. Patent Application No. 60/748,880, which was filed Dec. 8, 2005, and is incorporated herein by reference in its entirety.

FIELD OF THE INVENTION

The invention relates to cell culturing methods and media containing manganese that improve glycosylation or sialylation of glycoproteins, including erythropoietin and analogs or derivatives thereof.

BACKGROUND

Erythropoietin (EPO) is a glycoprotein hormone that is normally synthesized and secreted by peritubular cells in the kidney and functions as the principle homeostatic regulator of red blood cell production. Recombinant human erythropoietin (rHuEPO) is used clinically to treat anemias and increase red blood cell production in numerous different conditions, such as perisurgery, chronic renal failure, side effects of HIV or HCV treatment, and side effects of cancer chemotherapy. Pharmaceutical biosynthesis of glycoproteins such as EPO is complicated by the need for both high levels of expression and appropriate posttranslational processing, which involves the addition of N-linked and O-linked branched oligosaccharide chains.

In glycoproteins, sugars are attached either to the amide nitrogen atom in the side chain of asparagine (termed an N-linkage) or to the oxygen atom in the side chain of serine or threonine (termed an O-linkage). The process for forming N-linked carbohydrates begins with the addition of 14 monosaccharides to a lipid-linked dichol in the endoplasmic reticulum (ER). After its formation, this carbohydrate complex is then transferred to the protein by the oligosaccharyltransferase (OST) complex in a process termed "core glycosylation" in the ER. The oligosaccharyltransferase (OST) complex is a multi-protein unit comprised of ribophorin I, II, OST48 and DAD1 (Kelleher and Gilmore 1997 PNAS 94(10):4994-4999; Kelleher et al. 2003 Molecular Cell 12(1): 101-111; Kelleher et al. 1992 Cell 69(1):55-65).

Subsequently, the polypeptides are transported to the Golgi complex, where the O-linked sugar chains are added and the N-linked sugar chains are modified in many different ways. In the cis and medial compartments of the Golgi complex, the original 14-saccharide N-linked complex may be trimmed through removal of mannose (Man) residues and elongated through addition of N-acetylglucosamine (GlcNac) and/or fucose (Fuc) residues. The various forms of N-linked carbohydrates have in common a pentasaccharide core consisting of three mannose and two N-acetylglucosamine residues. Finally, in the trans Golgi, other GlcNac residues can be added, followed by galactose (Gal) and a terminal sialic acid (Sial). Carbohydrate processing in the Golgi complex is called "terminal glycosylation" to distinguish it from core glycosylation.

Sialic acid is a generic name for a family of about 30 naturally occurring acidic monosaccharides that are frequently the terminal sugars of carbohydrates found on glycoproteins and glycolipids. Sialylation of recombinant glycoproteins is very important and may impart many significant properties to the glycoprotein including charge, immunogenicity, resistance to protease degradation, plasma clearance rate, and bioactivity.

The final complex carbohydrate units can take on many forms, some of which have two, three or four branches (termed biantennary, triantennary or tetraantennary). An exemplary N-linked biantennary structure is shown below:

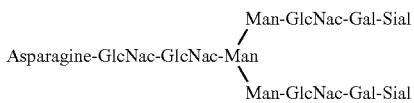

A number of enzymes involved in glycosylation utilize divalent cations as co-factors. For example, numerous enzymes involved in the dolichol-linked oligosaccharide synthesis require divalent cations as co-factors for activity (Couto et al. 1984 J. Biol. Chem. 259(1):378-382; Jensen and Schutzbach 1981 J. Biol. Chem. 256(24):12899-12904; Sharma et al. 1982 European Journal of Biochemistry 126(2): 319-25). The enzyme which catalyses the addition of O-linked carbohydrate to the polypeptide also requires a divalent cation for activity (Sugiura et al. 1982 J. Biol. Chem. 257(16):9501-9507). Manganese (Mn++) is a required co-factor for the enzyme β-galactoside-α-1,3,-galactosyltransferase, which catalyzes the addition of terminal galactose to elongating N-acetyl-glucosamine sugars (Witsell et al. 1990 J. Biol. Chem. 265(26):15731-7). It was previously reported that manganese at a concentration of 0.1 mM or 1 mM partially reversed the reduction in N-linked and O-linked occupancy of erythropoietin caused by A23187, a compound which depletes divalent cations (Kaufman et al. 1994 Biochemistry 33(33):9813-9).

rHuEPO has previously been shown to contain three N-linked and one O-linked branched carbohydrate structures that are highly sialylated (Takeuchi et al. 1988 J. Biol. Chem. 263(8):3657-3663). De-sialylated EPO is virtually inactive to induce erythropoiesis in vivo due to the rapid clearance of this modified protein by the hepatocyte asialo glycoprotein receptor (Ashwell and Harford 1982 Annual Review of Biochemistry 51(1):531-554; Goochee et al. 1991 Bio/Technology. 9(12):1347-55). Other studies have shown that sialylation and glycosylation decreases binding kinetics of EPO to the EPO receptor. (Darling et al. 2002 Biochemistry 41(49):14524-31.)

Darbepoetin alfa is a novel glycosylation analog of recombinant human erythropoietin (rHuEPO) that contains two additional N-linked glycosylation sites. Darbepoetin has decreased receptor-binding activity but exhibits a three-fold longer serum half-life and increased in vivo activity as a result of this increased persistence in circulation. The in vivo activity of EPO analogs has been demonstrated to correlate with the number of N-linked carbohydrates. (Elliott et al., Exp Hematol. 2004 32(12):1146-55.)

rHuEPO produced in CHO cells can exhibit a variable extent of glycosylation and sialylation. (Takeuchi et al., 1989 PNAS 86(20):7819-22, Zanette et al., 2003 Journal of Biotechnology 101(3):275-287). Given that EPO sialylation is an important factor in in vivo bioactivity, consistency in glycosylation and higher levels of sialylation of rHuEPO and its analogs are desirable qualities when producing recombinant protein for therapeutic uses. Thus, there exists a need for culture media and culturing methods that improve the glycosylation or sialylation of glycoproteins produced in cell cultures.

SUMMARY OF THE INVENTION

In one aspect, the invention provides culture media comprising host cells and a non-toxic amount of manganese effective to increase the sialylation of a glycoprotein composition produced by such host cells.

In another aspect, the invention provides methods for improving sialylation of glycoproteins by growing host cells producing such glycoproteins in a culture medium containing manganese, in an amount effective to increase the sialylation of such glycoproteins.

Exemplary glycoproteins include erythropoiesis-stimulating molecules, such as erythropoietin and darbepoetin. The manganese may be present in an amount effective to increase sialylation, either through increasing the percentage of sialylated molecules produced or through increasing their degree of sialylation, and/or effective to increase occupancy of O-linked or N-linked glycosylation sites, and/or effective to increase galactosylation. Preferably the addition of manganese to culture medium improves such a property(ies) by at least 10%, 20%, 30%, 40%, 50%, 60%, 70%, or more relative to culture media lacking manganese or culture media containing a lower concentration of manganese.

In one exemplary embodiment, the invention provides a method for producing an erythropoietic composition comprising sialylated erythropoiesis-stimulating molecules, wherein the method involves the step of growing a manganese-responsive host cell in culture medium containing manganese, and optionally includes the step of recovering an erythropoietic composition characterized by any one, two, three, four or more of the following improved properties: (1) a reduced percentage of "lower sialylated" erythropoiesis-stimulating molecules, e.g. less than about 5% of the molecules are lower sialylated; (2) an increased percentage of "highly sialylated" erythropoiesis-stimulating molecules; (3) an increased percentage of erythropoiesis-stimulating molecules which are glycosylated at potential O-linked glycosylation sites; (4) an increased percentage of galactose among the sugars attached to erythropoiesis-stimulating molecules, or (5) an increased percentage occupancy of potential N-linked glycosylation sites.

The manganese in the culture medium is at a concentration that is effective to provide one or more of such improved properties, e.g. ranging from about 0.01 to about 40 µM, from about 0.1 to about 10 µM, or from about 0.4 to about 4 µM.

In any of the preceding culture media or methods, the culture medium may be essentially serum-free and/or may optionally comprises one or more supplementary amino acids selected from the group consisting of asparagine, aspartic acid, cysteine, cystine, isoleucine, leucine, tryptophan, or valine.

The host cell may be any mammalian cell, e.g. a CHO cell, and may be grown in any suitable culture system, e.g. in roller bottles.

The manganese may be present in the initial growth medium or may be added after a rapid cell growth phase, e.g. a period ranging between about 2 and 20 days, or may be added after one or two harvest cycles.

Other features and advantages of the invention will become apparent from the following detailed description. It should be understood, however, that the detailed description and the specific examples, while indicating exemplary embodiments of the invention, are given by way of illustration only, because various changes and modifications within the spirit and scope of the invention will become apparent to those skilled in the art from this detailed description.

DETAILED DESCRIPTION OF THE INVENTION

Figure 1:
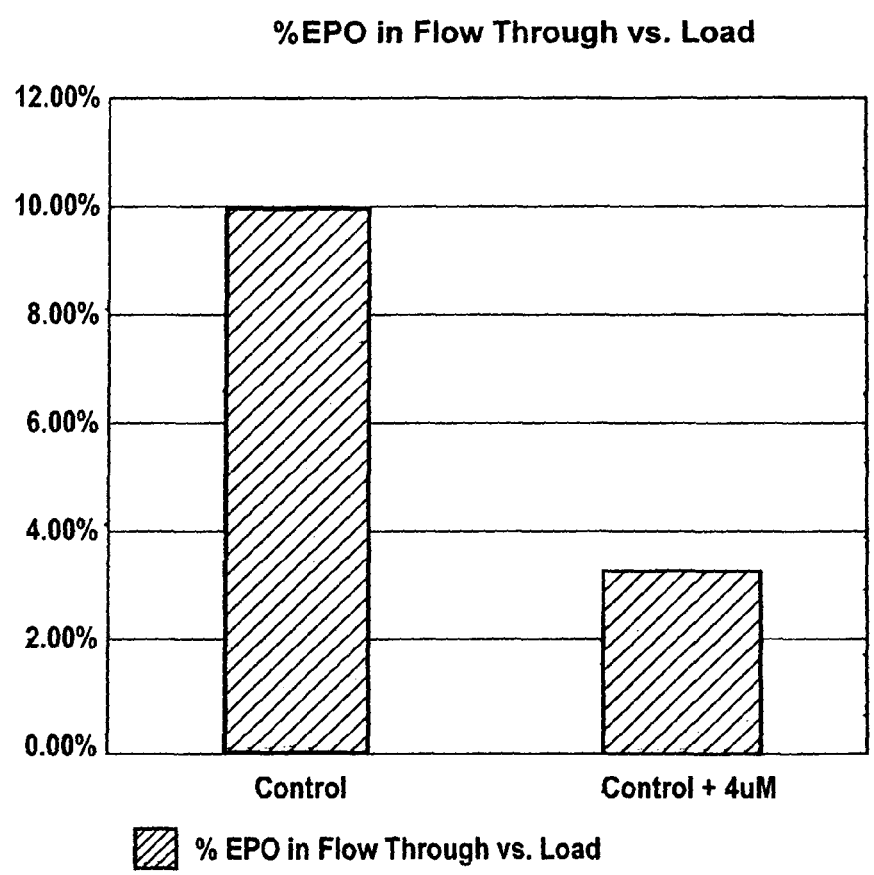
FIG. 1 displays the amount of rHuEPO in the flow through fraction as a percentage of the amount loaded onto the column and shows results from culture medium with no added manganese, and with 4 µM added manganese.

The invention provides culture media and cell culture methods that improve the sialylation of glycoproteins, particularly erythropoiesis-stimulating molecules such as erythropoietin of SEQ ID NO: 3, or analogs, variants, or derivatives thereof, including darbepoetin of SEQ ID NO: 2.

Recombinant glycoproteins produced in CHO cells can exhibit variable glycosylation and sialylation. Highly sialylated forms of glycoprotein molecules can be separated from lower sialylated (including non-sialylated) forms of such molecules via anion exchange chromatography. Sialic acids, being acidic and thus negatively charged, are captured on the column, so that highly sialylated molecules are retained on the column while lower sialylated forms flow through. The amount of glycoprotein in each fraction (retained on column vs. flow through fraction) can be determined and compared to the starting amount of glycoprotein loaded from the cell culture media.

The addition of manganese to culture medium has been shown herein to result in significant alterations in post-translational processing of erythropoiesis-stimulating molecules, such as erythropoietin and darbepoetin, by the cultured cells producing erythropoietin. Manganese decreases the amount of lower sialylated glycoprotein produced (and increases the amount of highly sialylated glycoprotein recovered), increases the number of potential O-linked glycosylation sites that are occupied by sugar chains, increases the number of potential N-linked glycosylation sites that are occupied by sugar chains, increases the terminal galactosylation of sugar chains, and increases terminal sialylation of sugar chains. Manganese did not appear to alter the degree of branching of the sugar chains (e.g. one, two, three or four branches). Manganese also reverses the reduction in sialylation observed when the culture medium is periodically supplemented with amino acids depleted during cell culture, e.g. asparagine, aspartic acid, cysteine, cystine, isoleucine, leucine, tryptophan, and valine.

The term "erythropoietic composition" as used herein means a collection of erythropoiesis stimulating molecules that contain glycosylation sites, and among which at least some of the molecules carry a sugar chain comprising at least one terminal sialic residue (i.e. such molecules are "sialylated"). Similarly, the term "glycoprotein composition" as used herein means a collection of glycoprotein molecules, among which at least some of the molecules are sialylated.

The term "erythropoiesis-stimulating molecules" as used herein includes human erythropoietin (SEQ ID NO.: 3) or a biologically active variant, derivative, or analog thereof, including a chemically modified derivative of such protein or analog. Amino acids 1 through 165 of SEQ ID NO: 3 constitute the mature protein. Another exemplary erythropoiesis-stimulating molecule is darbepoetin (SEQ ID NO: 2). Amino acids 1 through 165 of SEQ ID NO: 2 constitute the mature protein. Also contemplated are analogs of erythropoietin (SEQ ID NO.: 3) or darbepoetin (SEQ ID NO: 2), with 65%, 70%, 75%, 80%, 85%, 90%, 91%, 92%, 93%, 94%, 95%, 96%, 97%, 98%, or 99% homology to SEQ ID NO: 3 or SEQ ID NO: 2, respectively, and still retaining erythropoietic activity.

Exemplary sequences, manufacture, purification and use of recombinant human erythropoietin are described in a number of patent publications, including but not limited to Lin U.S. Pat. No. 4,703,008 and Lai et al. U.S. Pat. No. 4,667,016, each of which is incorporated herein by reference in its entirety. Darbepoetin is a hyperglycosylated erythropoietin analog having five changes in the amino acid sequence of rHuEPO which provide for two additional carbohydrate chains. More specifically, darbepoetin contains two additional N-linked carbohydrate chains at amino acid residues 30 and 88 of SEQ ID. NO: 2. Exemplary sequences, manufacture, purification and use of darbepoetin and other erythropoietin analogs are described in a number of patent publications, including Strickland et al., 91/05867, Elliott et al., WO 95/05465, Egrie et al., WO 00/24893, and Egrie et al. WO 01/81405, each of which is incorporated herein by reference in its entirety.

As used herein, "analogs" refers to an amino acid sequence that has insertions, deletions or substitutions relative to the parent sequence, while still substantially maintaining the biological activity of the parent sequence, as determined using biological assays known to one of skill in the art. "Variants" include naturally occurring allelic variants, splice variants, or polymorphic forms of the parent sequence. "Derivatives" of naturally occurring, variant or analog polypeptides include those which have been chemically modified, for example, to attach water soluble polymers (e.g., polyethylene glycol), radionuclides, or other diagnostic or targeting or therapeutic moieties, any of which can be attached directly or indirectly through linkers.

The term "erythropoietic activity" means activity to stimulate erythropoiesis as demonstrated in an in vivo assay, for example, the exhypoxic polycythermic mouse assay. See, e.g., Cotes and Bangham, *Nature*, 191:1065 (1961).

The term "manganese-responsive host cell" as used herein means a host cell which produces a glycoprotein and which responds to added manganese in its culture medium by increasing sialylation, either by increasing the percentage of sialylated glycoprotein molecules produced or by increasing the degree of sialylation (i.e. the number of sialic acids per molecule) of the glycoprotein molecules produced. For erythropoietic compositions, manganese-responsive host cells include host cells that respond to added manganese by increasing the percentage of highly sialylated erythropoiesis-stimulating molecules recovered after anion exchange chromatography carried out as described below. In exemplary embodiments, manganese-responsive host cells may include host cells growing anchored to a solid surface, e.g. in roller bottles. Any manganese-responsive host cells described herein may be used according to the invention.

Culture Medium Components

The invention provides a culture medium comprising an amount of manganese effective to increase the sialylation of a glycoprotein composition produced by cells grown in this culture medium. In one embodiment, said amount of manganese is non-toxic to the cells, i.e., does not reduce cell viability, cell growth or protein production. In related embodiments, the invention provides a culture medium comprising an amount of manganese effective to increase the sialylation of an erythropoietic composition produced by cells grown in this culture medium.

The amount of manganese in the culture media of the invention may be greater than the "trace element" amount present in standard media compositions, e.g., greater than 0.001 µM. While the quality of erythropoietic compositions is clearly improved by the addition of 40 µM manganese to host cell cultures, in some cases the yield of protein secreted into the media is substantially reduced, indicating a toxic effect of such a concentration of manganese. In exemplary embodiments, the concentration of manganese in the culture medium (i.e. the final concentration after the manganese-supplemented medium is added to the host cells in culture) ranges from about 0.01 to about 40 µM, or from about 0.1 to about 10 µM, or from about 0.4 to about 4 µM. In other exemplary embodiments, the concentration of manganese at the lower end of the desired range may range from about 0.005, 0.01, 0.05, 0.1, 0.2, 0.3, 0.4, 0.5, 0.6, 0.7, 0.8, 0.9, 1, 1.5, 2, 2.5, 3, 3.5 or 4 µM or higher; the concentration of manganese at the higher end of the range may also range up to about 50, 45, 40, 35, 30, 25, 20, 15, 10, 9, 8, 7, 6, 5 or 4 µM.

The concentration of manganese in the culture medium added to the cells may be adjusted to achieve the desired final concentration of manganese in the culture system. For example, with batch processes involving complete removal and replacement of culture medium, replacement culture medium containing 4 µM $Mn^{2+}$ is added to the cells to achieve a final culture medium at 4 µM $Mn^{2+}$. Alternatively, when continuous perfusion processes are used, the concentration of manganese in the added media will need to be higher to achieve a final culture medium at the desired $Mn^{2+}$ concentration within a range. Adjustment of the concentration can be easily carried out by one of ordinary skill in the art.

The culture medium can also include any other necessary or desirable ingredients known in the art, such as carbohydrates, including glucose, essential and/or non-essential amino acids, lipids and lipid precursors, nucleic acid precursors, vitamins, inorganic salts, trace elements including rare metals, and/or cell growth factors. The culture medium may be chemically defined or may include serum, plant hydrolysates, or other derived substances. The culture medium may be essentially or entirely serum-free or animal-component free. Essentially serum-free means that the medium lacks any serum or contains an insignificant amount of serum.

The culture medium may also include supplementary amino acids depleted during cell culture, e.g. asparagine, aspartic acid, cysteine, cystine, isoleucine, leucine, tryptophan, and valine. The amino acid supplementation may be in the initial growth medium and/or in medium added during or after the rapid growth phase.

The medium may include lipids and/or lipid precursors such as choline, ethanolamine, or phosphoethanolamine, cholesterol, fatty acids such as oleic acid, linoleic acid, linolenic acid, methyl esters, D-alpha-tocopherol, e.g. in acetate form, stearic acid; myristic acid, palmitic acid, palmitoleic acid; or arachidonic acid. A number of commercially available lipid mixtures are available.

The medium may include an iron supplement comprising iron and a synthetic transport molecule to which the iron binds. The medium may include inorganic compounds or trace elements, supplied as appropriate salts, such as sodium, calcium, potassium, magnesium, copper, iron, zinc, selenium, molybdenum, vanadium, manganese, nickel, silicon, tin, aluminum, barium, cadmium, chromium, cobalt, germanium, potassium, silver, rubidium, zirconium, fluoride, bromide, iodide and chloride. A number of commercially available mixtures of trace elements are available.

The medium may also optionally include a nonionic surfactant or surface-active agent to protect the cells from the mixing or aeration. The culture medium may also comprise buffers such as sodium bicarbonate, monobasic and dibasic phosphates, HEPES and/or Tris.

In exemplary embodiments, the media is DMEM/F-12 media (Gibco) containing 5% serum. DMEM includes the following inorganic salts: Calcium Chloride, Cupric sulfate Ferric-Nitrate or Sulfate, Potassium Chloride, Magnesium Sulfate or Chloride, Sodium Chloride, Sodium Dihydrogen Phosphate, Sodium Bicarbonate, Zinc sulfate; the following amino acids L-Alanine, L-Arginine, L-Asparagine, L-Aspartic acid, L-Cysteine, L-Glutamic acid, L-Glutamine, Glycine, L-Histidine, L-Isoleucine, L-Leucine, L-Lysine, L-Methionine, L-Phenylalanine, L-Proline, L-Serine, L-Threonine, L-Tryptophan, L-Tyrosine, L-Valine; the following lipids and vitamins: Biotin, D-Calcium-Pantothenate, Choline Chloride, Folic Acid, myo-Inositol, Niacinamide, Nicotinamide, Pyridoxine, Riboflavin, Thiamine, Vitamin B12 (cobalamin), Thymidine, Linoleic Acid, Lipoic Acid; and other components including D-Glucose, Phenol Red, Hypoxanthine, Sodium Pyruvate, Putrescine, and HEPES.

The culture medium may also comprise inducers of protein production, such as sodium butyrate, or caffeine. Other known inducers include, but are not limited to, the following compounds: N-Acetyl-L-cysteine, Actinomycin D, 7-Amino-, Bafilamycin A1, *Streptomyces griseus*, Calphostin C, *Cladosporium cladosporioides*, *Camptothecin*, *Camptotheca acuminata*, CAPE, 2-Chloro-2'-deoxyadenosine, 2-Chloro-2'-deoxyadenosine 5'-Triphosphate, Tetralithium Salt, Cycloheximide, Cyclophosphamide Monohydrate, Cyclosporine, *Trichoderma polysporum*, Daunorubicin, Hydrochloride, Dexamethasone, Doxorubicin, Hydrochloride, (−)-Epigallocatechin Gallate, Etoposide, Etoposide Phosphate, ET-18-OCH3, 5-Fluorouracil, H-7, Dihydrochloride, Genistein, 4-Hydroxynonenal, 4-Hydroxyphenylretinamide, Hydroxyurea, IL-1β Inhibitor, (±)-S-Nitroso-N-acetylpenicillamine, S-Nitrosoglutathione, Phorbol-12-myristate-13-acetate, Puromycin, Dihydrochloride, 1-Pyrrolidinecarbodithioic Acid, Ammonium Salt, Quercetin, Dihydrate, Rapamycin, Sodium Butyrate, Sodium 4-Phenylbutyrate, D-erythro-Sphingosine, N-Acetyl-, D-erythro-Sphingosine, N-Octanoyl-, Staurosporine, *Streptomyces* sp., Sulindac, Thapsigargin, TRAIL, *E. coli*, Trichostatin A, *Streptomyces* sp., (±)-Verapamil, Hydrochloride, Veratridine, Vitamin D3, 1α, 25-Dihydroxy-, and Vitamin E Succinate (VWR and Calbiochem).

The culture medium optionally excludes A23187 or other compounds which deplete divalent cations.

Culturing Methods

The invention also provides methods for producing a glycoprotein composition, such as an erythropoietic composition, which may include culturing a manganese-responsive host cell in any of the culture media described herein. Such methods may further include the step of recovering the glycoprotein composition, e.g. the erythropoietic composition, from the host cells or culture medium. Manganese may be included in the initial culture medium during the initial growth phase or may be added at later stages. Manganese may have a greater effect when added after a rapid growth phase during which maximum or near maximum host cell growth is achieved, for example, a period longer than 2, 3, 4, 5, 7, 10, 15 or 22 days, or up to 22, 25, 30, 35, 40, 45, 50, or 55 days and may have an even greater effect after prolonged cell growth, e.g. after two harvest cycles. When the recombinant protein is secreted into the medium, the medium can be harvested periodically, so that the same host cells can be used through several harvest cycles. In exemplary embodiments, host cells producing erythropoiesis-stimulating molecules are incubated in three discrete batch harvest cycles. For each cycle, medium is harvested and replaced with fresh medium. The first cycle may be, e.g., 8 days; the second cycle, e.g., 7 days; and the third cycle, e.g., 5 days in duration.

Any host cells known in the art to produce glycosylated proteins may be used, including yeast cells, plant cells, plants, insect cells, and mammalian cells. Exemplary yeast cells include *Pichia*, e.g. *P. pastoris*, and *Saccharomyces* e.g. *S. cerevisiae*, as well as *Schizosaccharomyces pombe*, *Kluyveromyces*, *K. Zactis*, *K. fragilis*, *K. bulgaricus*, *K. wickeramii*, *K. waltii*, *K. drosophilarum*, *K. thernotolerans*, and *K. marxianus*; *K. yarrowia*; *Trichoderma reesia*, *Neurospora crassa*, *Schwanniomyces*, *Schwanniomyces occidentalis*, *Neurospora*, *Penicillium*, *Totypocladium*, *Aspergillus*, *A. nidulans*, *A. niger*, *Hansenula*, *Candida*, *Kloeckera*, *Torulopsis*, and *Rhodotorula*. Exemplary insect cells include *Autographa californica* and *Spodoptera frugiperda*, and *Drosophila*. Exemplary mammalian cells include varieties of CHO, BHK, HEK-293, NS0, YB2/3, SP2/0, and human cells such as PER-C6 or HT1080, as well as VERO, HeLa, COS, MDCK, NIH3T3, Jurkat, Saos, PC-12, HCT 116, L929, Ltk-W138, CV1, TM4, W138, Hep G2, MMT, a leukemic cell line, embryonic stem cell or fertilized egg cell.

A variety of culture systems are known in the art, including T-flasks, spinner and shaker flasks, roller bottles and stirred-tank bioreactors. Roller bottle cultivation is generally carried out by seeding cells into roller bottles that are partially filled (e.g., to 10-30% of capacity) with medium and slowly rotated, allowing cells to attach to the sides of the bottles and grow to confluency. The cell medium is harvested by decanting the supernatant, which is replaced with fresh medium. Anchorage-dependent cells can also be cultivated on microcarrier, e.g. polymeric spheres, that are maintained in suspension in stirred-tank bioreactors. Alternatively, cells can be grown in single-cell suspension.

Culture medium may be added in a batch process, e.g. where culture medium is added once to the cells in a single batch, or in a fed batch process in which small batches of culture medium are periodically added. Medium can be harvested at the end of culture or several times during culture. Continuously perfused production processes are also known in the art, and involve continuous feeding of fresh medium into the culture, while the same volume is continuously withdrawn from the reactor. Perfused cultures generally achieve higher cell densities than batch cultures and can be maintained for weeks or months with repeated harvests.

Methods for controlling sialylation of a recombinant glycoprotein, particularly for controlling N-glycolylneuraminic acid (NGNA) levels in the sugar chains, are described in U.S. Pat. No. 5,459,031, incorporated herein by reference in its entirety, and such methods may be used in conjunction with the culture media and culture methods described herein. The methods involve adjusting culture parameters, including the carbon dioxide level, to achieve the desired NGNA content in carbohydrate.

Evaluation of Glycosylation and Sialylation

For glycoprotein compositions, an increase or improvement in sialylation can be determined by anion exchange chromatography according to Elliott et al., Biochemistry, 33(37):11237-45 (1994), herein incorporated by reference in its entirety. More highly sialylated proteins are expected to be more negatively charged and bind more strongly to the column, while less sialylated and asialoproteins flow through or are easily eluted. The amount of glycoprotein molecules in each of the two fractions (retained on resin vs. flow through fraction) can be determined, e.g., by ELISA, and compared to the starting amount of such molecules loaded from the cell culture media. Exemplary ELISA kits are sold commercially and include R & D Systems, IVD Human EPO EIA kit.

Chromatography is carried out as follows. To eliminate cells and debris, medium in which mammalian cells that produce an erythropoiesis-stimulating molecule, or other glycoprotein, have been cultured is centrifuged at about 1000 rpm and filtered through a 0.45 micron filter. This material is then subjected to anion exchange chromatography in order to prepurify a fraction containing primarily the four to seven most highly sialylated species of the glycoprotein molecules. A strong ion exchange resin may be used, such as, for example, TRICORN™ Mono-Q 5/50 GL (Amersham, part # 17-5166-01) or other strong anion exchange resins, particularly those that have the quaternary amine —$CH_2$—$N^+$—$(CH_3)_3$ as the functional group of the resin. The exact procedure will depend on the theoretical maximum number of sialic acid residues that the particular glycoprotein molecules can contain. For example, a theoretical maximum number of sialic acid residues for human erythropoietin, which has 3 N-glycan sites and 1 O-glycan site, is (3×4)+2=14. This assumes that each N-glycan site can have up to four branches (since pentaantennary species are rare) and that each O-glycan site can have up to two branches. Making similar assumptions for darbepoetin, which has 5 N-glycan sites and 1 O-glycan site, the theoretical maximum for darbepoetin is (5×4)+2=22. The buffers used to elute the glycoprotein molecules from the anion exchange column are designed to: (1) elute from the column most or all protein molecules belonging to species that are less sialylated than a group of species consisting of approximately the top third most highly sialylated species (for erythropoietin, the "highly sialylated" species are those having 9-14 sialic acid residues per protein molecule, and for darbepoetin the "highly sialylated" species are those having 17-22 sialic acid residues per protein molecule); (2) then elute protein molecules belonging to the four to seven most highly sialylated species, and (3) finally remove more highly charged species from the column, which may include glycoforms bearing sulfated N-glycans. Therefore, the exact composition of the wash and elution buffers can be adjusted according to the theoretical maximum number of sialic acid residues on the glycoprotein molecule. One of skill in the art can make such adjustments based on routine empirical optimization of column parameters and assaying the material coming off the column on analytical isoelectric focusing gels.

Analytical polyacrylamide isoelectric focusing gels that can separate different charged forms of erythropoiesis-stimulating molecules bearing different numbers of sialic acid residues can also be performed essentially as described in the Amersham-Pharmacia Guide to Isoelectric Focusing (APB, RW May 5, 1998) in 6 M urea using commercially available ampholytes (pH 3 to 5 for human erythropoietin or pH 2 to 4 for darbepoetin). Other pH ranges for ampholytes may be appropriate for other erythropoiesis-stimulating molecules with substantially different numbers of sialic acid residues.

For erythropoietin, the extent of sialylation is estimated by determining the percent of total erythropoietic protein loaded onto an anion exchange column that elutes in a fraction containing mostly highly sialylated species of erythropoietin having 9 to 14 sialic acid residues per protein molecule.

For darbepoetin, the extent of sialylation is estimated by determining the percent of total erythropoetic protein loaded onto an anion exchange column that elutes in a fraction containing mostly highly sialylated species of darbepoetin having 18 to 22 sialic acid residues per protein molecule.

An increase in the percentage of erythropoiesis-stimulating molecules recovered from the pool retained on the resin (or a reduction in the percentage of such molecules observed in the flow through fraction) relative to the control (e.g. produced from media with no manganese or trace element amounts of manganese) indicates an increase in sialylation, whether through increasing the percentage of sialylated molecules produced or through increasing their degree of sialylation.

The actual glycan structure can be determined by any techniques known in the art, including enzymatic digestion of carbohydrate, lectin immunoblotting, 1D and 2D 1H-NMR spectroscopy, mass spectroscopy techniques including electrospray ionization tandem mass spectrometry (ESI MS) or matrix assisted laser desorption ionization time-of-flight mass spectrometry (MALDI-TOF MS), and/or fluorescent labeling of enzymatically released N-glycans followed by resolution by HPLC and comparison to known N-glycan control samples.

An exemplary technique, described in the examples below, for determining the amount of glycoprotein with an occupied O-glycosylation site involves N-Glycanase digestion to remove the N-linked carbohydrates followed by reverse phase-HPLC to separate the glycoprotein composition into two peaks. Peak identification as occupied O-site or unoccupied O-site can be confirmed by mass spectrometry.

N-site branching and sialylation, including the percentage of sialylated molecules produced and the degree of sialylation of the sialylated molecules, can be determined by analyzing the glycoproteins for structural content by N-glycan mapping and enzymatic sequencing, e.g. by digestion with N-Glycanase and neuraminidase, coupled with MALDI-TOF mass spectrometry for size determination of the released sugars. An exemplary technique is described in the examples below.

The percent of the sugars attached to the erythropoiesis-stimulating molecules that are galactose can be determined, e.g., by neuraminidase plus galactosidase digestion followed by HPLC separation or MALDI-TOF mass spectrometry for size determination of the released sugars. An exemplary technique is described in the examples below.

EXAMPLES

Example 1

Protein Production Methods

This example describes a cell culture method for production of recombinant human erythropoietin (rHuEPO, SEQ ID NO: 3) or darbepoetin (SEQ ID NO: 2). A DHFR minus CHO cell line was stably transfected with a genomic DNA sequence containing the human erythropoietin gene (Lin U.S. Pat. No. 4,703,008, incorporated herein by reference) or a cDNA sequence encoding darbepoetin gene (SEQ ID NO: 1). Roller bottles (850 cm$^2$) were inoculated with $1.7 \times 10^7$ total cells and grown for 5 days in 450 mls of 1:1 DMEM/F-12 media (Gibco) containing 5% serum. The cultures were washed once with PBS and then incubated in three discrete batch harvest cycles. Media was replaced twice in the first 14 days; the third cycle was 5 to 6 days in duration. For erythropoietin, at each harvest, the conditioned culture medium was completely removed and fresh 1:1 DMEM/F-12 without serum ("Standard Media") was added to replace the harvested media. When manganese was included in the culture medium, manganese chloride (Sigma) was added to all replacement culture media at the desired concentration, e.g. 0.4, 4 or 40 μM. Roller bottles were overlaid with a gas mix containing 80 torr $pCO_2$, 130 torr $pO_2$, and balanced $N_2$ after each media addition. Cells producing darbepoetin were cultured under conditions similar to cells producing erythropoietin except that the Standard Media was 2×1:1 DMEM/F-12 (without serum).

Example 2

Quantitation of rHuEPO or Darbepoetin in Harvested Culture Media

200 μl of harvested media produced according to Example 1 was analyzed for the amount of rHuEPO or darbepoetin produced, using reverse phase HPLC. Samples were separated on a polymer PLRPS (4.6 mm×150 mm; 1000 Å (Polymer Laboratories) under reverse phase conditions (linear AB gradient from 30%-55% B over 17 minutes; buffer A: 0.1% TFA in $H_2O$, buffer B: 0.1% TFA in 90% $CH_3CN$ (Sigma)). The retention time for rHuEPO or darbepoetin within the culture media was compared with a purified rHuEPO or darbepoetin standard (Amgen Inc.). Waters Millennium Software was used to manually integrate the rHuEPO or darbepoetin peak areas to ensure consistent integration. Integrated peak areas of unknown samples were quantitated by comparison to a known standard curve.

Example 3

Effect of Manganese on Highly Sialylated and Lower Sialylated Forms of Erythropoiesis-Stimulating Molecules CHO cells producing rHuEPO were grown as described in Example 1 with and without added 4 μM $MnCl_2$. Conditioned media collected after the third harvest cycle was analyzed for percent recovery of highly sialylated forms of rHuEPO. CHO cells producing darbepoetin were grown as described in Example 1 with and without added 4 μM $MnCl_2$. Conditioned media collected after each of the three harvest cycles was analyzed.

Lower sialylated forms of rHuEPO were separated from highly sialylated material using anion exchange method as described in Elliott et al., Biochemistry, 33(37):11237-45 (1994), herein incorporated by reference in its entirety. Briefly, highly sialylated rHuEPO, having a strong negative charge, binds to the resin while lower sialylated rHuEPO washes through the column. Cell culture media from each roller bottle obtained as described in Example 1 was first concentrated sixty-fold, to about 5-15 mg/mL, using a 10,000 MWCO membrane then buffer exchanged into 10 mM Tris pH 7.0. This concentrated and buffer exchanged media was loaded onto a strong anion exchange column having a quaternary amine as the functional group. Unbound material that flowed through at 10 mM Tris or eluted with low salt was collected as the lower sialylated fraction. Material bound to the ion exchange (IEX) column was eluted with higher salt as the "recoverable" highly sialylated fraction.

The total amount of rHuEPO in one or both fractions was measured using an ELISA kit obtained from R&D Systems (Quantikine IVD Human EPO EIA kit), following the manufacturer's recommended procedure, and compared to the total amount of rHuEPO in the harvest media loaded onto the column. Dilutions of 1:1,000,000 and 1:500,000 of each flow-through sample were made prior to analysis in order to fall within the standard curve of the assay. A highly sialylated fraction of darbepoetin was separated using similar methods as described above to isolate the isoforms with 17-22 sialic acid residues and measured using RP-HPLC.

Figure 2:
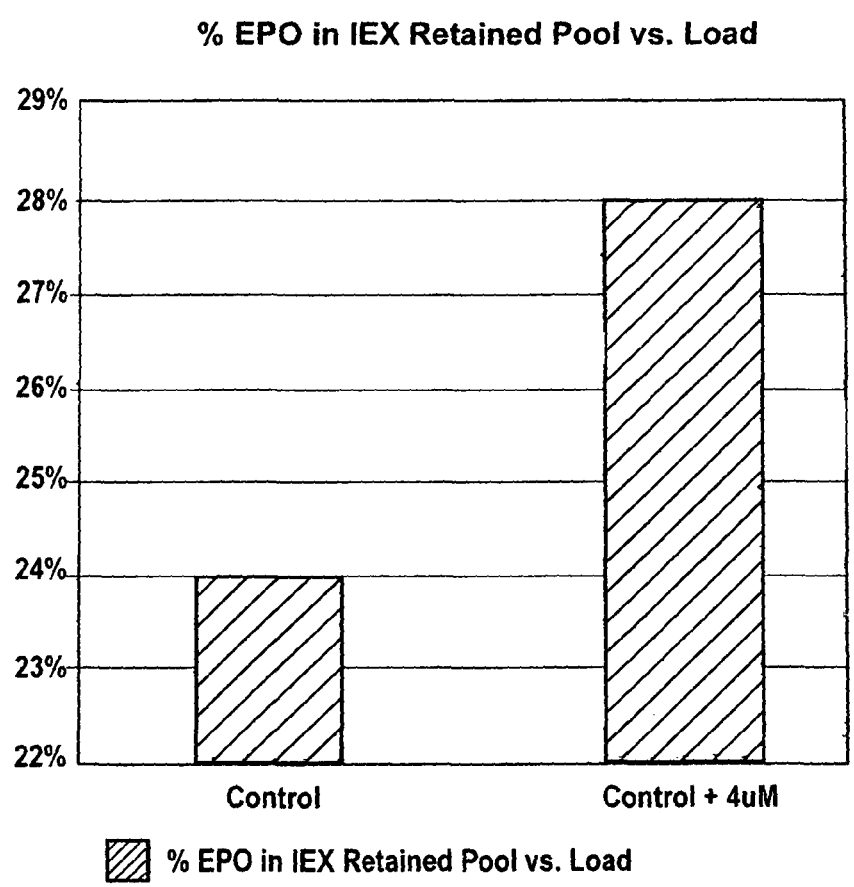
FIG. 2 displays the amount of rHuEPO in the IEX-retained fraction as a percentage of the amount loaded onto the column and shows results from culture medium with no added manganese, and with 4 µM added manganese.

Results of a representative experiment for rHuEPO are shown in FIGS. 1 and 2. FIG. 1 displays the amount of rHuEPO in the flow through fraction as a percentage of the amount loaded onto the column and shows that the addition of 4 μM manganese reduced the lower sialylated fraction of EPO compared to control, from 10.01% to 3.39%. FIG. 2 displays the amount of rHuEPO in the IEX-retained fraction as a percentage of the amount loaded onto the column and shows that the addition of 4 μM manganese increased the percent recoverable EPO in the highly sialylated fraction compared to control, from 24% to 28%.

Figure 3:
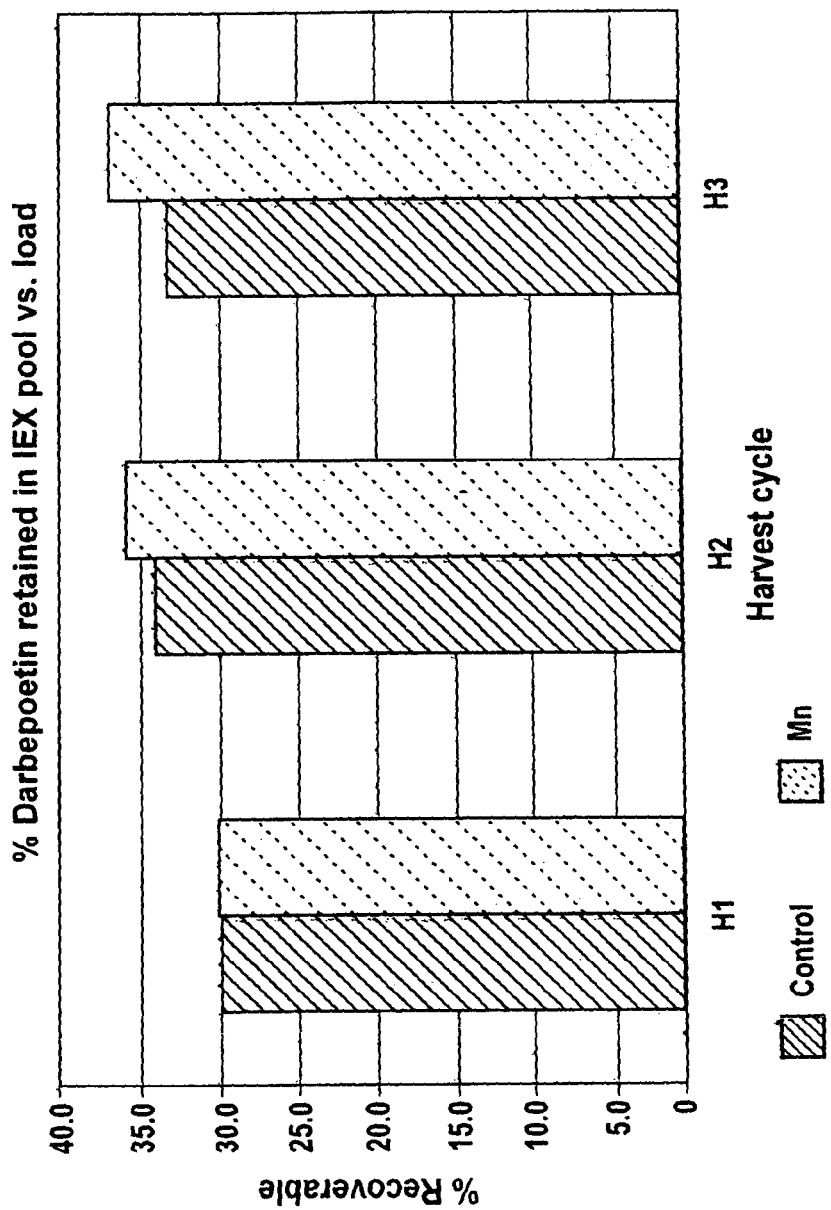
FIG. 3 displays the amount of darbepoetin in the IEX-retained fraction as a percentage of the amount loaded onto the column, after each harvest cycle, and shows results from culture medium with no added manganese, and with 4 µM added manganese.

Results of a representative experiment for darbepoetin are shown in FIG. 3. FIG. 3 displays data from each harvest cycle and shows that the addition of 4 μM manganese increased the percent recoverable darbepoetin in the highly sialylated fraction compared to control, from 32.8% to 36.3% after the third harvest. The further addition of 7 mM N-acetylmannosamine appeared to provide a further increase in % recoverable darbepoetin to 41.1% after the third harvest.

These data demonstrate that addition of $Mn^{2+}$ to culture medium decreased production of lower sialylated forms of erythropoietin and darbepoetin in CHO cell cultures, and increased percent of recoverable highly sialylated forms.

In experiments carried out with a line of CHO cells adapted for growth in suspension culture in large tanks and or CHO cells adapted to suspension culture in serum-free medium, no effect of manganese on the fraction of lower sialylated darbepoetin was observed.

Example 4 rHuEPO O-Site Characterization

CHO cells producing rHuEPO were grown as described in Example 1 with and without added 4 μM $MgCl_2$. Un-fractionated culture media collected after the third harvest cycle was analyzed for percent O-site occupancy of rHuEPO. CHO cells producing darbepoetin were grown as described in Example 1 with and without added 4 μM $MgCl_2$. Conditioned media collected after each of the three harvest cycles was analyzed. CHO cells producing darbepoetin were also grown as described in Example 1 with 0.4, 1, 4, 10 and 40 μM $MgCl_2$ and media from the third harvest cycle was analyzed.

The percentage of O-linked sites occupied with glycosylation was quantified by first removing N-linked structures by N-Glycanase (Sigma) digestion of the cell culture media, followed by reverse phase HPLC chromatography. Specifically, 5 U of N-Glycanase (Sigma) was added to 10 μL of concentrated (1:60) culture media samples and digested at 37° C. for three hours. The samples were then analyzed by reverse phase chromatography using a Zorbax C-8 column (150 mm×2.1 mm (VWR) using a linear AB gradient from 35%-60% B over 30 minutes (buffer A: 0.1% TFA in $H_2O$, buffer B: 0.1% TFA in 90% $CH_3CN$ (Sigma)). The resulting chromatogram separates rHuEPO into two peaks; the first peak corresponds to the occupied O-site rHuEPO peptide while the smaller, second peak corresponds to the unoccupied O-site rHuEPO peptide.

To confirm that these two peaks represented occupied and unoccupied O-sites, fractions corresponding to these peaks were collected and compared to N-Glycanase digested purified rHuEPO (Amgen Inc.). SDS-PAGE analysis showed that N-Glycanase digestion reduces the apparent molecular weight of rHuEPO from 32 kDal to a doublet with a major component of 18.5 kDal and a slightly faster migrating minor component. The larger peak migrated with the larger N-Glycanase digested rHuEPO band while the minor peak migrated with the smaller rHuEPO band. Lys-C peptide mapping in combination with mass spectrometry confirmed that the larger peak corresponds to rHuEPO containing an O-linked carbohydrate while the smaller peak corresponds to rHuEPO devoid of an O-linked carbohydrate.

Figure 4:
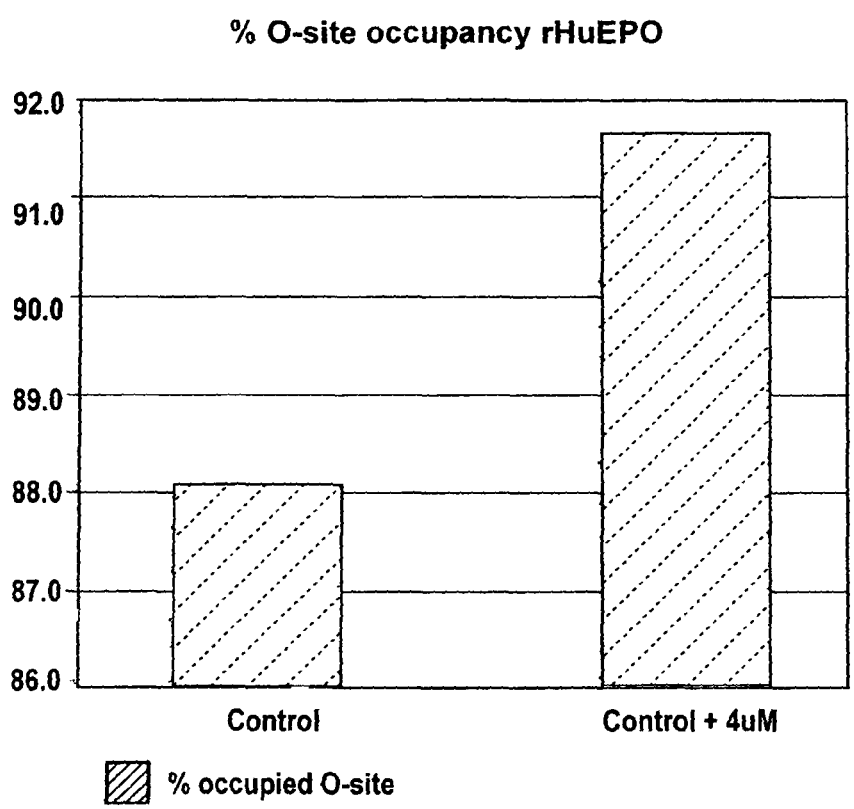
FIG. 4 displays percent of rHuEPO molecules in which O-sites were occupied with glycosylation and shows results from culture medium with no added manganese, and with 4 µM added manganese.

Results of a representative experiment analyzing O-site occupancy for rHuEPO are displayed in FIG. 4. FIG. 4 shows that the addition of 4 μM manganese increased the rHuEPO O-site occupancy compared to control, from 88.1% to 91.6%.

Figure 5:
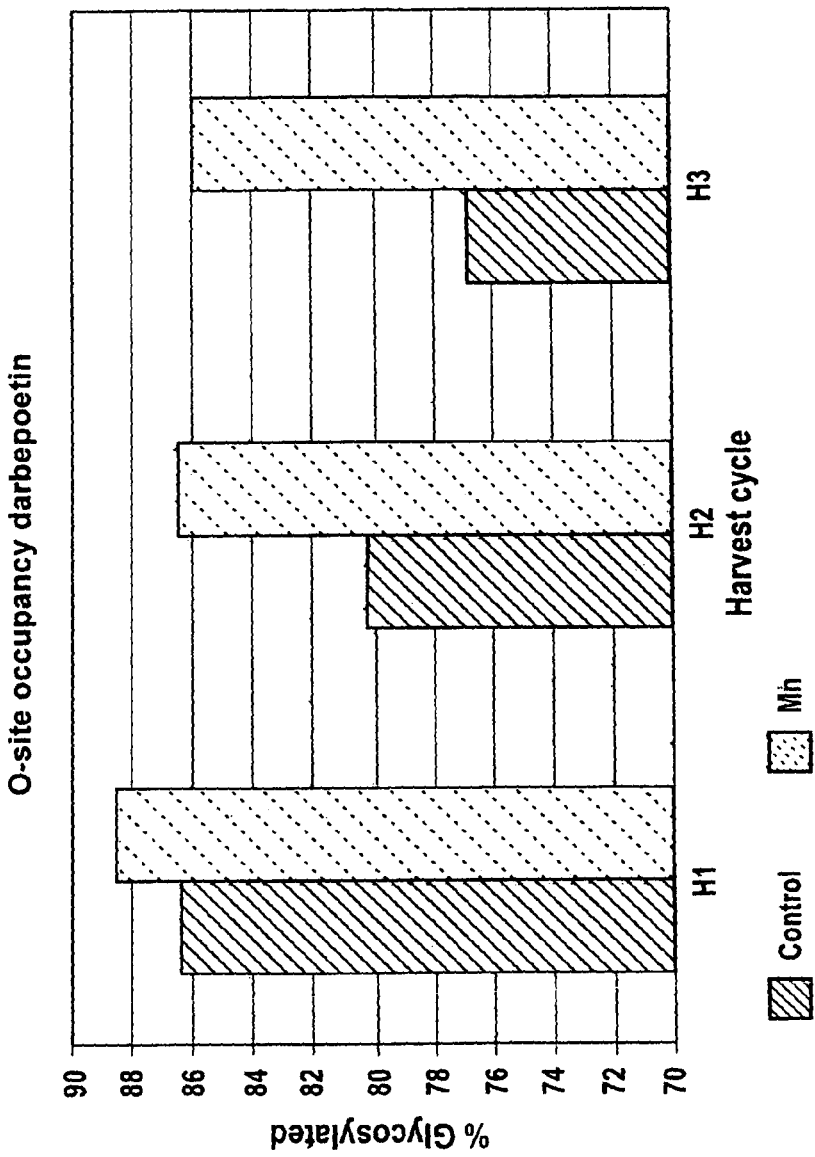
FIG. 5 displays percent of darbepoetin molecules in which O-sites were occupied with glycosylation, after each harvest cycle, and shows results from culture medium with no added manganese, and with 4 µM added manganese.
Figure 6:
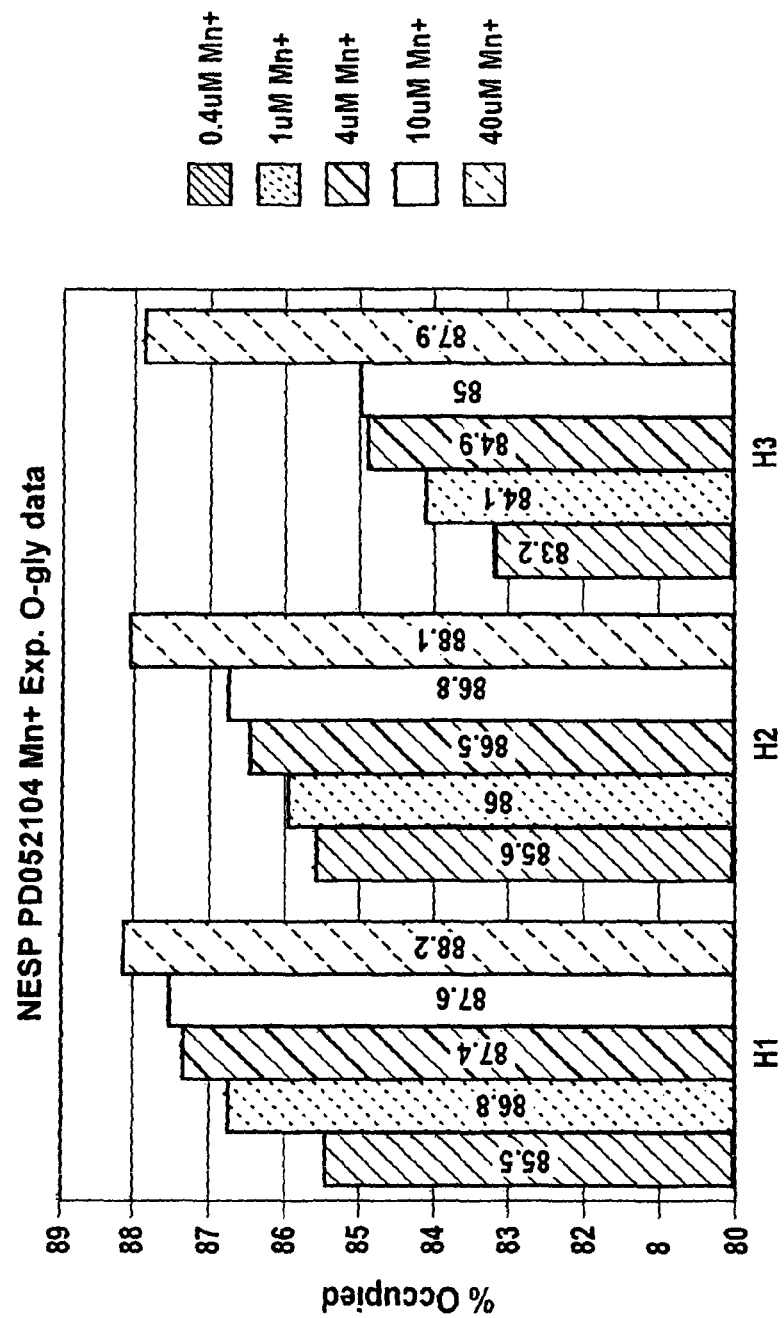
FIG. 6 displays percent of darbepoetin molecules in which O-sites were occupied with glycosylation and shows results from culture medium with varying concentrations of manganese.

Results of representative experiments for darbepoetin are displayed in FIGS. 5 and 6. FIG. 5 shows data from each harvest cycle and demonstrates that the addition of 4 μM manganese increased the darbepoetin O-site occupancy compared to control, from 76.8% to 86% after the third harvest. FIG. 6 displays data from the third harvest cycle for darbepoetin and shows that O-site occupancy increased with increasing concentrations of manganese. However, 40 μM manganese adversely affected levels of protein production, resulting in a total relative decrease of 17% in the mg of darbepoetin produced over the three harvest cycles combined. In contrast, 10 μM manganese did not appear to substantially affect protein production.

These data demonstrate that addition of $Mn^{2+}$ to culture medium increases O-site occupancy for erythropoietin and darbepoetin produced in CHO cell cultures.

Example 5

Evaluation of rHuEPO N-site Branching and N-Site Occupancy

To determine N-site branching of rHuEPO or darbepoetin produced according to Example 1, the lower sialylated fractions are analyzed for structural content by N-glycan mapping and enzymatic sequencing coupled with MALDI-TOF mass spectrometry for size determination. Briefly, the procedure calls for the N-glycans to be enzymatically released with 1 U/mL N-Glycanase (Sigma), then desalted and deproteinated using PGC chromatography (VWR). The free N-glycans are labeled at the reducing terminus with a fluorescent tag 2-aminobenzamide (2AB) by reductive amination (Sigma). A second cleanup procedure is performed utilizing paper chromatography (VWR). The $^{2AB}$N-glycan pools are mapped on a Dionex PA1 column with fluorescence detection (excitation 330 nm, emission 420 nm) using a sodium acetate gradient of 50-150 mM at 1.67 mM/min with sodium hydroxide (Sigma) at 50 mM isocratic. The $^{2AB}$N-glycan pools are desilylated using 1 U/mL A. ureafaciens neuraminidase with and without 0.5 U/mL B. testes galactosidase. All digests are performed at 37° C. for 18 h. Additional size analysis of all the $^{2AB}$N-glycan pools is obtained by MALDI-TOF mass spectrometry (Voyager, Applied BioSystems). The matrix is saturated 2,5-dihydroxy benzoic acid in 70% acetonitrile, 0.05% TFA (Sigma) and mixed at a 1:1 ratio with the 2AB N-glycan pool on the probe. The MALDI settings are as follows: Accelerating voltage: 20,000 V; Grid voltage: 94%; Guide wire: 0.05%; Extraction delay time: 75 nsec; Laser intensity: 2300; Mass range: 500-5000.

To determine the N-linked occupancy of rHuEPO, 10 μg of a rHuEPO standard (Amgen Inc.) is digested with 0.04 U of N-Glycanase (Sigma) overnight at room temperature to give a molecular weight ladder of rHuEPO with varying N-linked occupied forms. 0.1 μg of total rHuEPO collected from harvest media is loaded and separated by SDS-PAGE (Novex, Invitrogen) and then transferred to PVDF. Blots are probed with a monoclonal antibody to rHuEPO.

Example 6

Effect of Amino Acid Supplementation on rHuEPO Production and Glycosylation

To determine the effect of addition of amino acids on production of rHuEPO during cell culture, the levels of all twenty amino acids were determined by amino acid analysis in the starting media ("Standard Media" of Example 1) and then again after five days of incubation in the third harvest cycle as described in above in Example 1. Nine specific amino acids (non-essential and essential) were depleted to low levels (<3 mg/L) over this culture period: cysteine, isoleucine, leucine, tryptophan, valine, asparagine, aspartic acid, glutamate, and glutamine. The concentrations of these 8 amino acids in standard media were doubled to create enriched media. Enriched Medium consisted of serum-free 1:1 DMEM/F-12 media supplemented with 1% amino acid stock (2.25 g/L asparagine; 1.99 g/L aspartic acid; 1.76 g/L cysteine; 3.13 g/L cystine; 2.21 g/L glutamic acid; 5.45 g/L isoleucine; 5.91 g/L leucine; 0.90 g/L tryptophan; and 5.29 g/L valine). Cells were cultured in either Standard Media or in Enriched Media, which was used throughout the entire twenty-one day culture process. After the third harvest cycle, media was collected and rHuEPO in the harvested media was quantitated by reversed phase HPLC.

CHO cells cultured in Enriched Media showed a modest increase of 12% in rHuEPO production compared to control cells cultured in Standard Media. However, although the Enriched Media improved rHuEPO protein production, the amount of lower sialylated material was increased two-fold, leading to an overall decrease in highly sialylated rHuEPO as compared to control cultures.

The change in the amount of rHuEPO found in the lower sialylated pool was due to a lower degree of sialylation of the individual carbohydrates rather than a lower degree of carbohydrate branching. The structures of N-linked carbohydrates found on rHuEPO in the lower sialylated fractions were analyzed by MALDI-TOF. Results are displayed below in Table 1 below.

TABLE 1

Results of MALDI-TOF analysis of rHuEPO N-Glycan lower sialylated pools.

| Structure[a] | Composition[b] | | | | Theoretical Mass[c] | Observed Masses[d] | | | | | | | | |
|---|---|---|---|---|---|---|---|---|---|---|---|---|---|---|
| | | | | | | Control | | | +Amino Acids | | | +Amino Acids + Mn++ | | |
| | Hex | HexN | dHex | Neu | | None | AUN | AUN + Gal | None | AUN | AUN + Gal | None | AUN | AUN + Gal |
| A | 2 | 2 | 1 | | 1036 | 1038 | 1038 | 1037 | 1039 | 1036 | 1038 | | | |
| B | 3 | 2 | 1 | | 1198 | 1200 | 1200 | 1198 | | | | | | |
| C | 2 | 3 | 1 | | 1239 | 1240 | 1239 | 1238 | 1241 | 1238 | 1240 | | | |
| D | 5 | 2 | | | 1376 | 1377 | 1379 | 1375 | 1378 | 1380 | 1374 | 1382 | 1375 | 1376 |
| E | 3 | 3 | 1 | | 1401 | 1403 | 1402 | 1401 | 1403 | 1401 | 1402 | | | 1401 |
| F | 4 | 3 | 1 | | 1563 | 1564 | 1562 | | 1564 | 1562 | | 1566 | 1562 | |
| G | 3 | 4 | 1 | | 1604 | 1605 | 1604 | 1604 | 1606 | 1604 | 1604 | | | 1604 |
| H | 4 | 4 | 1 | | 1766 | 1766 | 1766 | | 1767 | 1766 | | 1769 | 1765 | |
| I | 3 | 5 | 1 | | 1807 | 1807 | 1806 | 1806 | 1809 | 1806 | 1807 | | | 1807 |
| J | 5 | 4 | 1 | | 1928 | 1929 | 1927 | | 1929 | 1927 | | 1930 | 1927 | |
| K | 4 | 5 | 1 | | 1970 | 1970 | 1968 | | 1970 | 1968 | | | | |
| L | 3 | 6 | 1 | | 2011 | | | 2009 | 2011 | 2008 | 2009 | | | 2009 |
| M | 5 | 5 | 1 | | 2132 | 2130 | 2129 | | 2132 | 2129 | | | | |
| N | 4 | 6 | 1 | | 2173 | 2172 | 2170 | | 2172 | 2169 | | | | |
| O | 5 | 4 | 1 | 1 | 2220 | | | | | | | 2221 | | |
| P | 6 | 5 | 1 | | 2294 | 2292 | 2291 | | 2293 | 2291 | | | 2291 | |
| Q | 5 | 6 | 1 | | 2335 | 2331 | 2331 | | 2334 | 2332 | | | | |
| R | 6 | 6 | 1 | | 2497 | 2495 | 2493 | | 2495 | 2492 | | | | |
| S | 5 | 4 | 1 | 2 | 2511 | | | | | | | 2512 | | |
| T | 7 | 6 | 1 | | 2659 | 2656 | 2655 | | 2657 | 2655 | | | 2657 | |

[a]Structures A-T identified in FIG. 3 based on observed masses and general pathway of N-glycan biosynthesis.
[b]Hex, HexN, dHex and Neu indicate hexose, N-acetylhexosamine, deoxyhexose and N-acetyl neuraminic acid, respectively.
[c]Theoretical masses are calculated based on the average mass for the sodium adduct of a 2-aminobenzamide oligosaccharide with the indicated composition
[d]Observed masses for native (None), neuraminidase (AUN), and β-galactosidase (Gal) treated glycan's are given.

Figure 7:
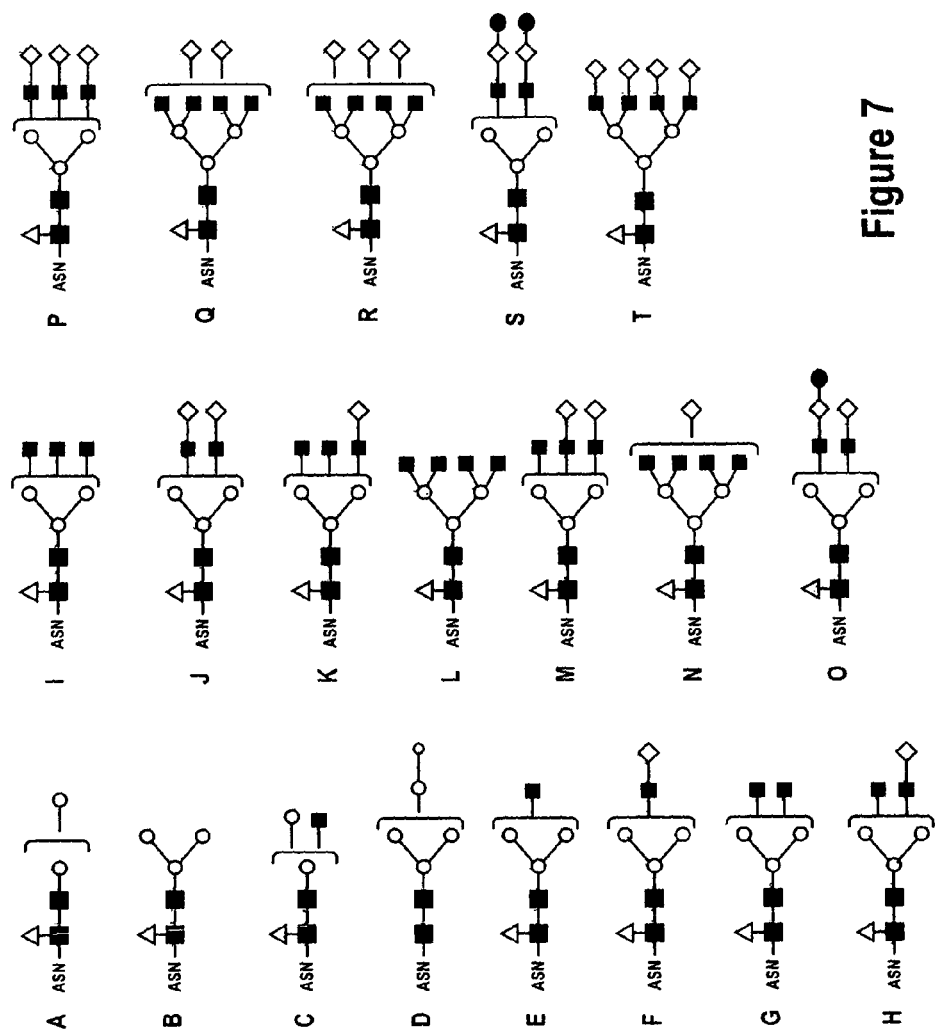
FIG. 7 shows representative glycosylation forms identified by MALDI-TOF MS.

In order to confirm some of the masses seen by MALDI-TOF, the lower sialylated fraction was digested with either neuraminidase, or neuraminidase and galactosidase. Masses representing highly branched carbohydrate structures were analyzed and compared between the control cultures grown in Standard Media and the cultures grown in the presence of Enriched Media. Masses representing highly branched carbohydrate structures (FIG. 7; structures M-T) were observed. Amino acid supplementation in the Enriched Media resulted in a mass corresponding to a highly branched structure that is missing all of its terminal galactose (FIG. 7, structure L). Similar masses of branched structures missing galactose were detected in both the control and Enriched Media cultures (FIG. 7, structures E, G-T, K, M-N, Q-R). These data indicate that the degree of branching in rHuEPO produced in Standard Media and Enriched Media is similar and suggests that the loss of sialic acid residues may be due to decreased galactosylation of highly branched N-linked carbohydrates.

Example 7

Manganese Reversed Effects of Amino Acid Supplementation on Glycosylation rHuEPO was cultured according to Example 1 in Enriched Media alone or Enriched Media plus 0.4, 4 and 40 μM $MnCl_2$. At early points in the culture; when cell numbers are low and the metabolic load is minimal, the Enriched Media has no effect on rHuEPO glycosylation. However, restoration of these depleted pools eventually caused defects in both oligosaccharide occupancy and sialylation, after the third harvest cycle.

Figure 8:
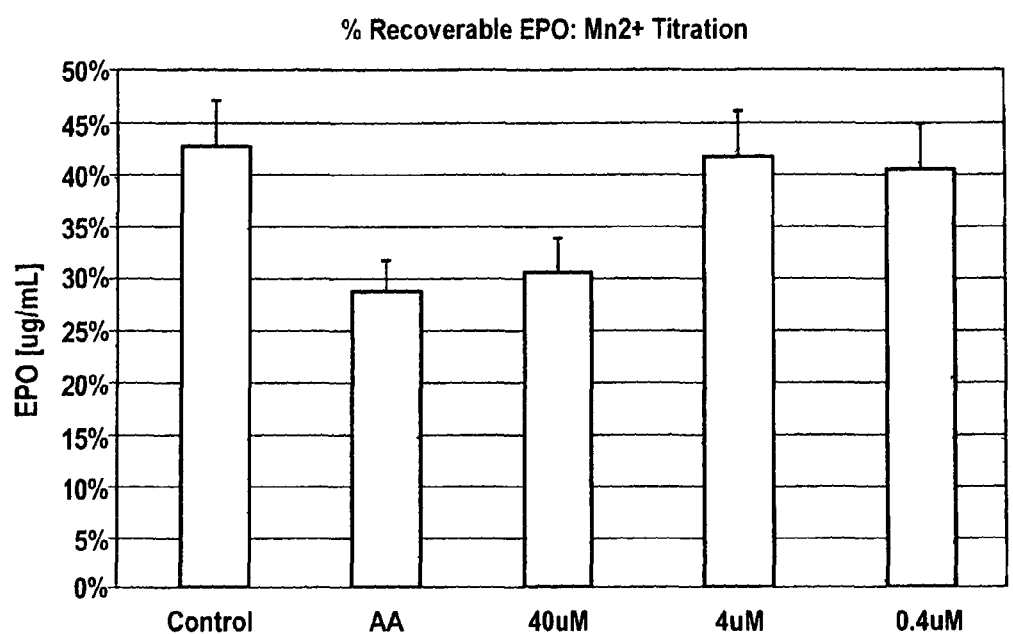
FIG. 8 displays percent of recoverable highly sialylated rHuEPO obtained after culturing in Standard Media, Enriched Media (Standard Media supplemented with amino acids), and Enriched Media with varying concentrations of manganese.
Figure 9:
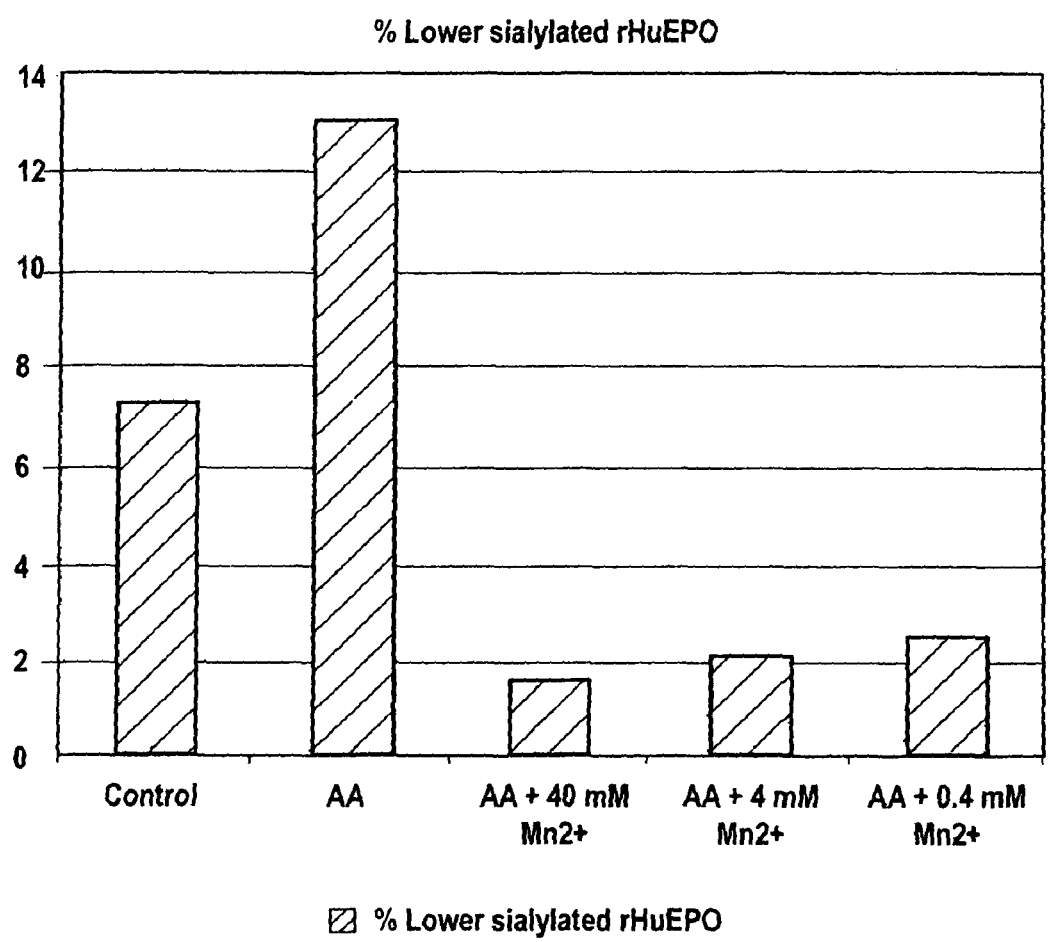
FIG. 9 displays the percent of lower sialylated rHuEPO forms obtained after culturing in Standard Media, Enriched Media, and Enriched Media with varying concentrations of manganese.
Figure 10:
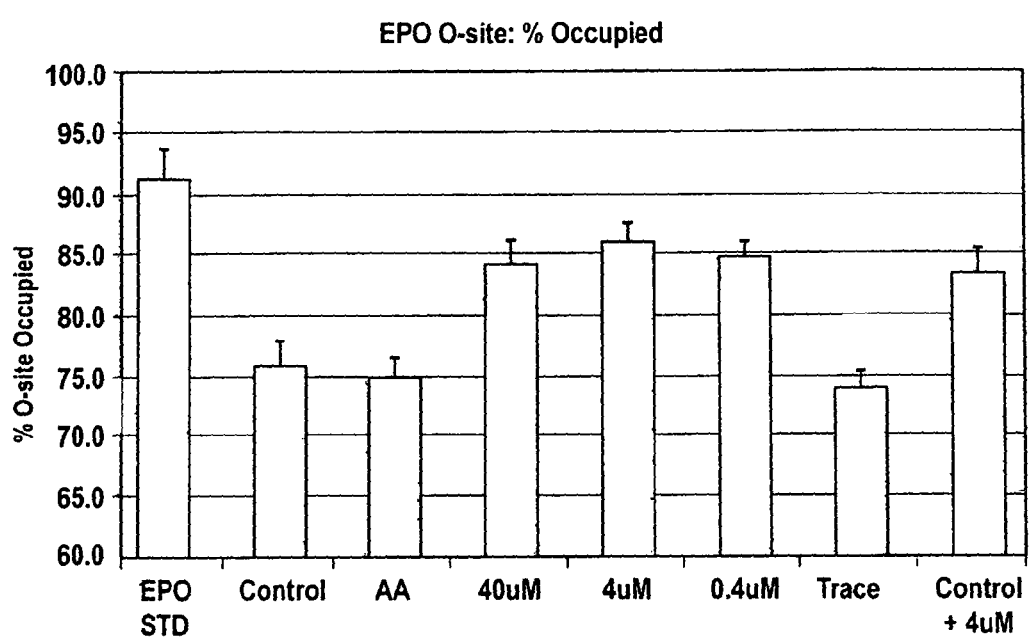
FIG. 10 displays percentage of O-site occupancy by glycosylation obtained after culturing in Standard Media, Enriched Media, and Enriched Media with varying concentrations of manganese.

Results of various representative experiments are shown in FIGS. 9, 10 and 11. FIG. 8 shows that culturing host cells in Enriched Media (supplemented with amino acids) reduced the percent of recoverable highly sialylated rHuEPO (43%, control vs. 29%, with amino acid supplementation). FIG. 8 also shows that adding manganese to the Enriched Media at 40, 4 and 0.4 μM improved percent recovery (31% at 40 μM, 42% at 4 μM, 41% at 0.4 μM).

FIG. 9 shows that culturing host cells in Enriched Media (supplemented with amino acids) increased the percent of lower sialylated rHuEPO forms obtained (7.3%, control vs. 13%, with amino acid supplementation). FIG. 9 also shows that adding manganese to Enriched Media greatly reduced the percent of lower sialylated rHuEPO produced at all concentrations of $Mn^{2+}$ (1.6% at 40 μM, 2.1% at 4 μM, and 2.4% at 0.4 μM).

FIG. 10 shows that culturing host cells in Enriched Media (supplemented with amino acids) reduces the percentage of O-site occupancy by sugar chains (76.2% control vs. 74.8% with amino acid supplementation). FIG. 10 also shows that adding manganese to Enriched Media increased the percentage occupancy of O-sites (84.4% at 40 μMm, 86.1% at 4 μM, 84.6% at 0.4 μM).

While the quality of rHuEPO was clearly improved by the addition of 40 μM $Mn^{2+}$ to cultures, the yield of rHuEPO protein secreted into the media was substantially reduced at this concentration of $Mn^{2+}$ (to 36% of control at 40 μM $Mn^{2+}$). Protein production levels remained high when concentrations of 4 and 0.4 μM $Mn^{2+}$ were added to Enriched Media (109 and 114% of control, respectively).

Additionally, the addition of $Mn^{2+}$ resulted in masses consistent with branched sugars containing fully galactosylated forms. Further digestion with neuraminidase plus galactosidase confirmed these results as masses were obtained consistent with core structures missing the galactose residues. Within the lower sialylated rHuEPO pool, the addition of $Mn^{2+}$ resulted in predominantly biantennary structures whereas the control and enriched amino acid media contained higher branched N-Glycans structures missing terminal galactose as described above (FIG. 7; structures H, J, O, S).

To rule out a possible limitation of the donor sugar nucleotide UDP-Gal as a cause for reduced galactosylation each condition was also assayed for relative quantities of UDP-Gal. The data show that the levels of UDP-Gal in each condition were statistically indistinguishable and therefore, not the cause for reduced galactosylation seen upon amino acid supplementation in Enriched Media. Nor was UDP-Gal availability a factor in the improvement of galactosylation seen after $Mn^{2+}$ addition.

Thus, the data show that $Mn^{2+}$ addition to the Enriched Medium, at all concentrations of $Mn^{2+}$, markedly reduced the fraction of lower sialylated rHuEPO produced and increased recovery of highly sialylated rHuEPO forms. The effects on sialylation were shown to increase with increasing concentrations of manganese in a dose-dependent manner. Manganese addition also improved rHuEPO galactosylation in the lower sialylated fraction, and increased O-linked occupancy. The improvement in glycosylation was independent of the level of rHuEPO production. Evaluation of N-site occupancy by Western blot as described in Example 5 also suggested that $Mn^{2+}$ addition improved N-site occupancy.

All publications, patents and patent applications cited in this specification are herein incorporated by reference in their entirety, including but not limited to the material relevant for the reason cited, as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for producing an erythropoietic composition comprising sialylated erythropoiesis-stimulating molecules, wherein said erythropoiesis-stimulating molecules comprise analogs of erythropoietin (SEQ ID NO:3) or darbepoetin (SEQ ID NO:2) with 75% homology to SEQ ID NO:3 or SEQ ID NO:2, respectively, and still retaining erythropoietic activity, comprising the steps of: growing a manganese-responsive host cell transfected with DNA encoding said analog in a culture medium containing an amount of manganese effective to increase the percentage of sialylated molecules or degree of sialylation of said erythropoietic composition, wherein the concentration of manganese in said culture medium ranges from about 0.01 to about 40 µM; and recovering said erythropoietic composition, wherein less than about 5% of the erythropoiesis-stimulating molecules are lower sialylated.

2. The method of claim 1 in which the amount of manganese is effective to increase the percentage of highly sialylated erythropoiesis-stimulating molecules.

3. The method of claim 1 wherein the amount of manganese is effective to increase the percentage of erythropoiesis-stimulating molecules which are glycosylated at potential O-linked glycosylation sites.

4. The method of claim 1 wherein the amount of manganese is effective to increase the percentage of galactose among the sugars attached to erythropoiesis-stimulating molecules.

5. The method of any one of claims 1 and 2-4 wherein the culture medium is essentially serum-free.

6. The method of any one of claims 1 and 2-4 wherein the erythropoiesis-stimulating molecules comprise the amino acid sequence of SEQ ID NO: 3 (erythropoietin) or erythropoietic fragments thereof.

7. The method of any one of claims 1 and 2-4 wherein the erythropoiesis-stimulating molecules comprise the amino acid sequence of SEQ ID NO: 2 (darbepoetin) or erythropoietic fragments thereof.

8. The method of any one of claims 1 and 2-4 wherein the host cell is a mammalian cell.

9. The method of claim 8 wherein the host cell is a CHO cell.

10. The method of any one of claims 1 and 2-4 wherein the manganese is at a concentration of from about 0.1 to about 10 µM.

11. The method of claim 10 wherein the manganese is at a concentration of from about 0.4 to about 4 µM.

12. The method of any one of claims 1 and 2-4 wherein the culture medium further comprises one or more supplementary amino acids selected from the group consisting of asparagine, aspartic acid, cysteine, cystine, isoleucine, leucine, tryptophan, or valine.

13. The method of any one of claims 1 and 2-4 wherein the host cells are grown in roller bottles.

14. The method of any one of claims 1 and 2-4 wherein the manganese is added after a rapid cell growth phase.

15. The method of claim 14 wherein the rapid cell growth phase lasts for a period ranging between about 2 and 20 days.

16. The method of claim 15 wherein the manganese is added after two harvest cycles.

17. The method of claim 16 wherein the first harvest cycle is about 8 days and the second harvest cycle is about 7 days long.

* * * * *